United States Patent [19]
Schoffstall

[11] Patent Number: 4,700,696
[45] Date of Patent: Oct. 20, 1987

[54] METHOD AND APPARATUS FOR APPLYING TRACTION

[76] Inventor: Charles D. Schoffstall, P.O. Box 195, Strausstown, Pa. 19559

[21] Appl. No.: 840,360

[22] Filed: Mar. 17, 1986

[51] Int. Cl.$^{4}$ .................................... A61F 5/00
[52] U.S. Cl. .................................... 128/71; 280/613
[58] Field of Search ............... 128/75, 71, 84 R, 84 C, 128/87 B, 581; 36/136, 132, 113–117, 1, 183; 280/613; 269/322, 323, 328

[56] References Cited

U.S. PATENT DOCUMENTS

| | | | |
|---|---|---|---|
| 2,583,895 | 1/1952 | Siebrandt | 128/84 R |
| 2,638,091 | 5/1953 | Varco . | |
| 2,773,499 | 12/1956 | Nieden . | |
| 2,796,061 | 6/1957 | Miller . | |
| 2,861,565 | 11/1958 | Lapierre | 128/71 |
| 2,997,250 | 8/1961 | Collins . | |
| 3,105,489 | 10/1963 | Zivi . | |
| 3,134,379 | 5/1964 | Nightingale . | |
| 3,221,735 | 12/1965 | Goodman et al. . | |
| 3,570,479 | 3/1971 | Horn . | |
| 3,602,501 | 8/1971 | Garner . | |
| 3,662,750 | 3/1972 | Jorgensen . | |
| 3,734,088 | 5/1973 | Tucker, Jr. et al. | 128/75 |
| 3,856,003 | 12/1974 | Pfluger | 128/75 |
| 3,905,190 | 9/1975 | Pearlman | 59/93 |
| 4,103,681 | 8/1978 | Shanley . | |
| 4,177,584 | 12/1979 | Beyl | 280/613 X |
| 4,185,851 | 1/1980 | Salomon | 280/613 |
| 4,391,443 | 7/1983 | Beecroft . | |
| 4,432,356 | 2/1984 | Sarrell et al. | 128/75 |
| 4,502,682 | 3/1985 | Miller . | |
| 4,503,845 | 3/1985 | Licciardi . | |
| 4,517,913 | 5/1985 | Albertini et al. | 59/84 X |
| 4,606,333 | 8/1986 | Graham | 128/75 |
| 4,627,422 | 12/1986 | Bates | 128/75 X |

*Primary Examiner*—Clifford D. Crowder
*Attorney, Agent, or Firm*—Caesar, Rivise, Bernstein, Cohen & Pokotilow, Ltd.

[57] ABSTRACT

A method and apparatus for applying traction therapy to an individual by supporting the individual on a body supporting platform inclined relative to a horizontal plane, with the individual sloping downwardly in a direction from his or her feet to his or her head. Traction applying means is connected to a harness which, in turn in connected to the upper portion of the individual's body to apply a force to the harness in the downwardly sloping direction of the platform, whereby traction is applied to the individual's body by a portion of the individual's body weight and by the weight applied through the harness. The invention also relates to securing means for retaining an individual on the traction device and safety means for preventing an individual from applying an excessive traction force to himself or herself.

32 Claims, 7 Drawing Figures

METHOD AND APPARATUS FOR APPLYING TRACTION

BACKGROUND OF THE INVENTION

This invention relates to method and apparatus for applying traction to parts of the human body.

A variety of systems are known in the art for applying traction to various parts of the human body. In applying such traction it has been suggested to position the patient in an inclined orientation on a supporting platform. Systems for supporting a patient in this manner are disclosed in the U.S. Pat. Nos. to Varco, 2,638,091; Horn, 3,570,479 and Shanley, 4,103,681.

In the devices disclosed in the Shanley patent and the Horn patent the body weight of the individual undergoing traction is the only weight or force relied upon to provide traction therapy. In other words, the sole purpose of the Shanley and Horn devices is to support an individual in an inclined orientation, and thereby take advantage of the individuals body weight to provide the desired traction therapy.

The Varco patent is directed to a pelvic traction belt assembly for the treatment of low back injuries. The individual undergoing traction therapy is supported on a inclined bed, with his or her head located lower than his or her feet. A tension force is applied through the pelvic traction belt by weights attached to the belt through a cord trained over a pulley located at the foot of the bed. Thus, in the Varco system the force applied to the individual through the traction belt is in a generally upwardly inclined direction, toward the individuals feet.

An additional traction device employing a rotatable and adjustable body supporting platform is disclosed in U.S. Pat. No. 2,773,499, issued to Nieden. Although Nieden describes a system wherein the platform is adjustable about pivots 14 or 15, he does not disclose a preferred angular orientation of the platform when traction therapy is applied to an individual through the use of a head harness. Moreover, when a head harness is employed a pair of cushioned positioning members 60 are located adjacent the shoulders to confine the traction force principally to the neck area. In other words, the Nieden arrangement is not designed to apply traction therapy to the entire spine.

The U.S. Pat. Nos. to Miller, 4,502,682, and Licciardi, 4,503,845, disclose body weight support devices intended to support a user in a completely inverted position. These devices can be extremely difficult to use, particularly by individuals who have either a back or neck problem.

The prior art also discloses a number of systems for providing a visual indication of the amount of traction force being applied to a patient. For example, note U.S. Pat. Nos. 3,105,489 (Zivi); 3,134,379 (Nightingale); 3,221,735 (Goodman et al.) and 3,662,750 (Jorgensen).

A number of patents disclose boots and other foot retaining systems for use in connecting an individual's feet to a piece of equipment. In this regard note U.S. Pat. Nos. 2,796,061 (Miller); 4,391,443 (Beecroft) and 3,602,501 (Garner).

Although the Beecroft boot construction includes an equipment attachment device located between raised heel and toe plates, it is not adapted for use in securing an individual on a traction table while, at the same time, permitting the desired degree of body movement relative to the line of traction force for assisting in controlling the location of the body to which the traction force is applied most predominantly.

U.S. Pat. No. 2,997,250, issued to Collins, discloses a portable traction device that employs a clock-type spring designed to apply up to a maximum of about 25 lbs. of traction force to a user thereof. Although a device such as disclosed in Collins may work satisfactorily to limit the maximum tension that can be applied to an individual, a need is believe to exist for a simpler arrangement to prevent an undesirably high traction force from being applied to an individual undergoing traction therapy.

OBJECTS OF THE INVENTION

It is a general object of this invention to provide method and apparatus for applying traction therapy in an easy, safe and reliable manner.

It is a further object of this invention to provide method and apparatus for applying traction therapy capable of treating the entire spinal area of a patient.

It is a further object of this invention to provide for patient mobility relative to the line along which the traction force is being applied so that the traction force can be applied most predominently to different selected locations of the spine.

It is a further object of this invention to provide method and apparatus for applying traction therapy to restore the lordotic curve in the spine.

It is a further object of this invention to provide method and apparatus for permitting a patient to be easily positioned and retained in an inclined position for receiving traction therapy.

It is a further object of this invention to provide a traction apparatus which can be easily operated by a patient undergoing traction therapy.

It is a further object of this invention to provide for the easy attachment of an individual on a platform of a traction device for permitting the individual to undergo traction therapy while being supported in an inclined position on said platform.

SUMMARY OF THE INVENTION

The above and other objects of this invention are achieved by supporting an individual to receive traction therapy on a body supporting platform that is inclined relative to a horizontal plane, with the individual slooping downwardly in a direction from his or her feet to his or her head, and applying a predetermined force through a harness attached to an upper portion of the individuals body in the downwardly sloping direction while maintaining the individual's feet secured against downward linear movement on the platform, whereby traction is applied to the individual by a portion of the individual's body weight and by the predetermined force applied through the harness.

Traction devices of this invention for permitting an individual to receive traction therapy while disposed in an inclined orientation include a body supporting platform, pivot means for mounting said platform to a fixed support and table adjustment means for adjusting the angular position of said platform by moving said platform about said pivot means. The devices include a cable assembly having one end connected to a body engaging member and a second end adapted to be secured to a traction actuating means for applying a traction force to the body engaging member through the cable assembly.

In one embodiment of the device the traction actuating means includes a drum rotatably supported on a collapsible drum-support. The cable attached to the body engaging member is trained about the drum, whereby force is applied to the body engaging member through the cable assembly by rotation of the drum. In this embodiment of the device the rotatable drum is movable between a first, active position, in which the drum is easily rotated by the patient while he or she is supported on the platform to thereby permit the patient to self-administer traction therapy, to a second, collapsed position to make it easier for the patient to position himself or herself on the platform than when the drum is in its first, active position.

In an alternate embodiment of this invention the traction actuating means is an electronic actuator that is operated from a control panel to apply the traction force to the cable assembly. In this embodiment a sensing module is included in the circuit for detecting the tension force being applied to the patient and for transmitting a signal representative of that force to a visual display device on the control panel.

In connection with the most preferred embodiments of this invention a safety tension link is included in the cable assembly and is adapted to break when a predetermined force is exceeded to prevent a force above said predetermined force from being imparted to the individual undergoing traction therapy.

Also in accordance with this invention means are provided for securing the patient's feet to the platform to thereby prevent downward movement of the patient when the platform is disposed in an inclined orientation with his or her head below his or her feet. The means for securing the feet to the platform includes a unique boot construction to be worn by the patient and including an elongate member projecting outwardly from the lower surface thereof. Gripping means are located on the traction device adjacent to the body-supporting platform for gripping the elongate member of each boot to retain the patient on the platform. Actuating means easily reachable by an individual undergoing traction therapy is provided for releasing the gripping means, and thereby disengaging the boots.

In the most preferred embodiment of this invention the elongate member projecting from each boot has a generally cylindrical section and the gripping means includes relatively moveable jaw members for encircling said generally cylindrical section for permitting rotational movement of each of the boots about the axis of said generally cylindrical section.

In the most preferred construction of the boot the elongate member projects outwardly from the lower surface thereof in a region between a toe member and heel member with the toe and heel members extending outwardly beyond the end of the elongate member. This arrangement permits a wearer of the boots to walk to the traction table without the elongate member engaging and thereby possibly damaging the ground or floor.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENTS OF THE INVENTION

Figure 1:
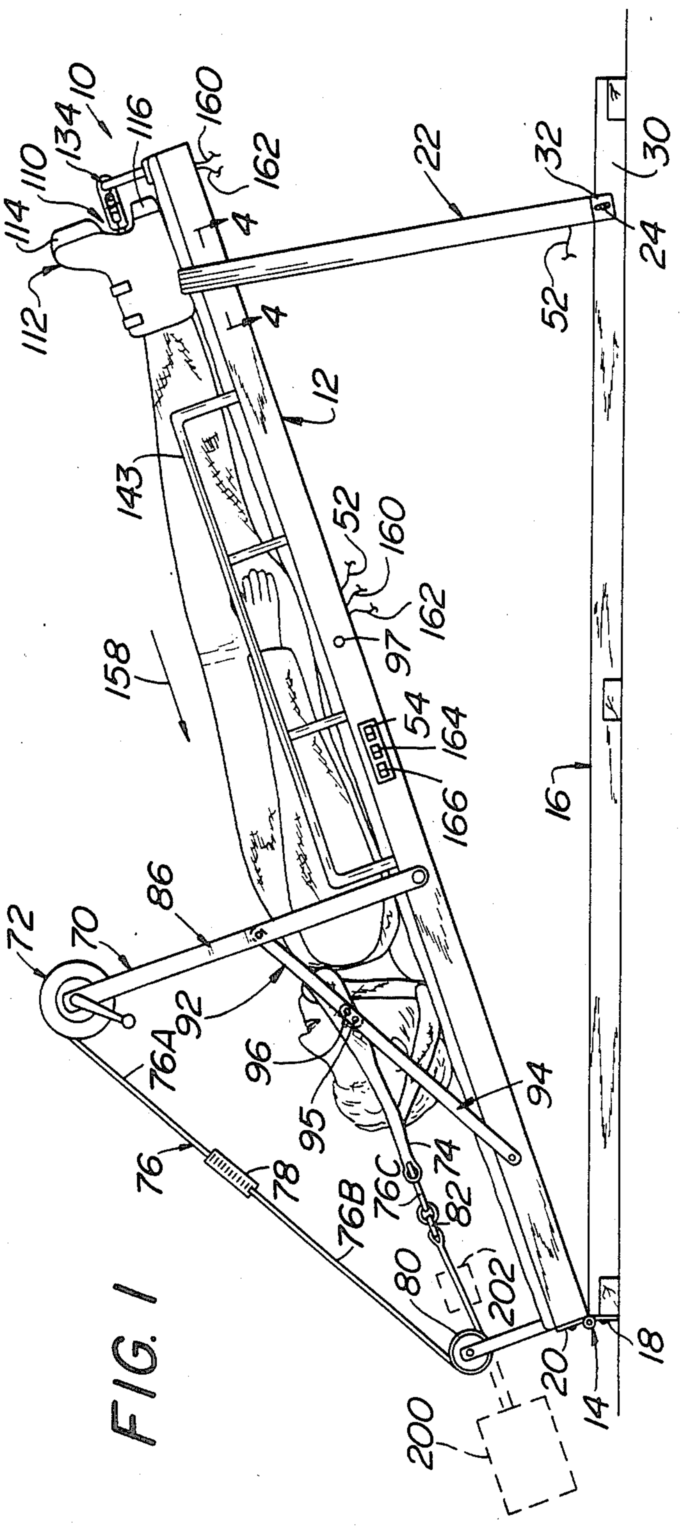
FIG. 1 is a side elevational view of a traction device in accordance with this invention, and with an individual receiving traction therapy thereon in accordance with a preferred method of this invention, and further wherein features of an alternate embodiment of a traction device is shown in phantom representation.

Referring now in greater detail to the various figures of the drawings wherein like reference characters refer to like parts, an adjustable traction device embodying the present invention is generally shown at 10 in FIG. 1. The device 10 basically comprises an adjustable body supporting platform 12 movable about a hinge 14. The hinge is secured to a lower horizontal support 16 adjacent an end 18 thereof, and also to the adjustable platform 12 adjacent an end 20 thereof.

Figure 3:
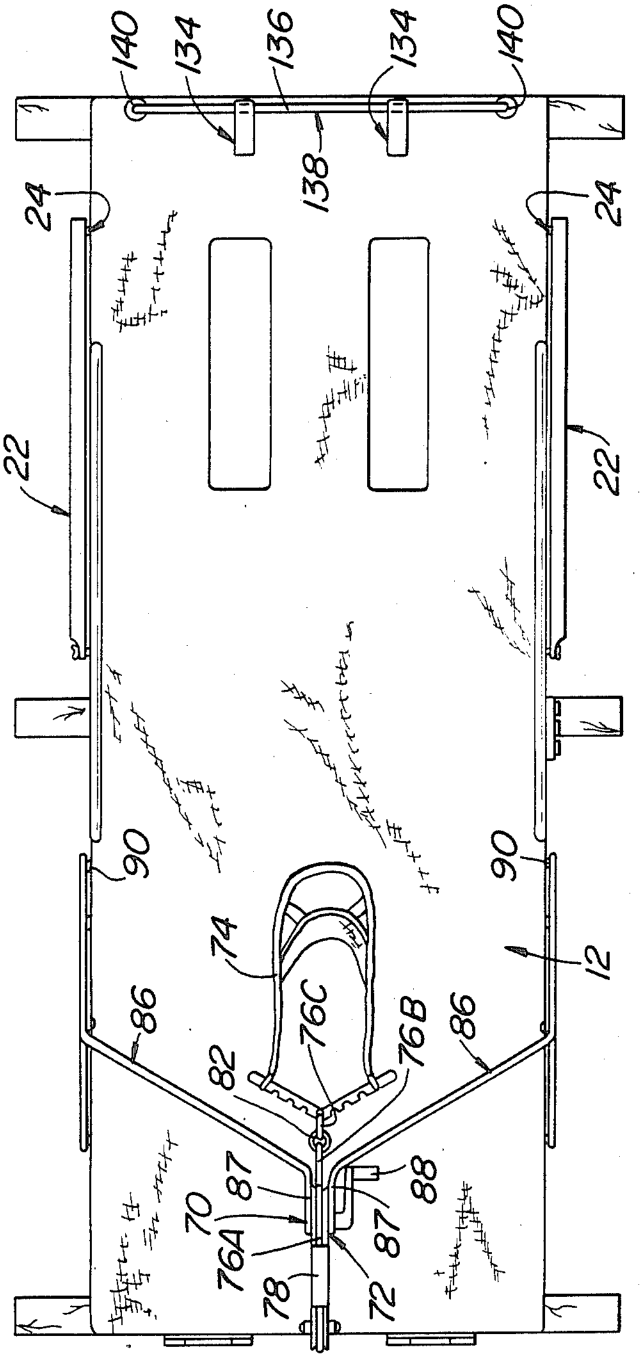
FIG. 3 is a plan view of the device illustrated in FIG. 2.

Referring to FIGS. 1 and 3, laterally spaced apart elongate table adjustment members 22 are removably attachable to the horizontal support 16 through a pivot connection 24, and are permanently secured to the body supporting platform 12 by means to be described in detail hereinafter. It is through the adjustment members 22 that the platform 12 is pivoted into its desired angular orientation relative to support 16 for applying traction therapy to a patient.

Figure 4:
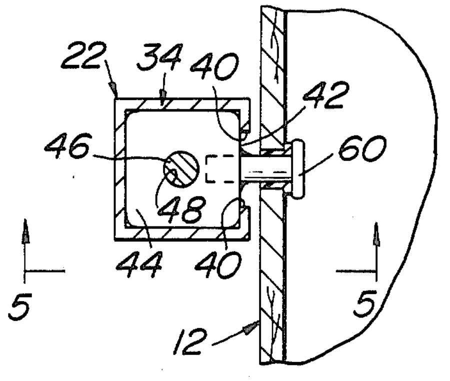
FIG. 4 is a sectional view taken along line 4—4 of FIG. 1.
Figure 5:
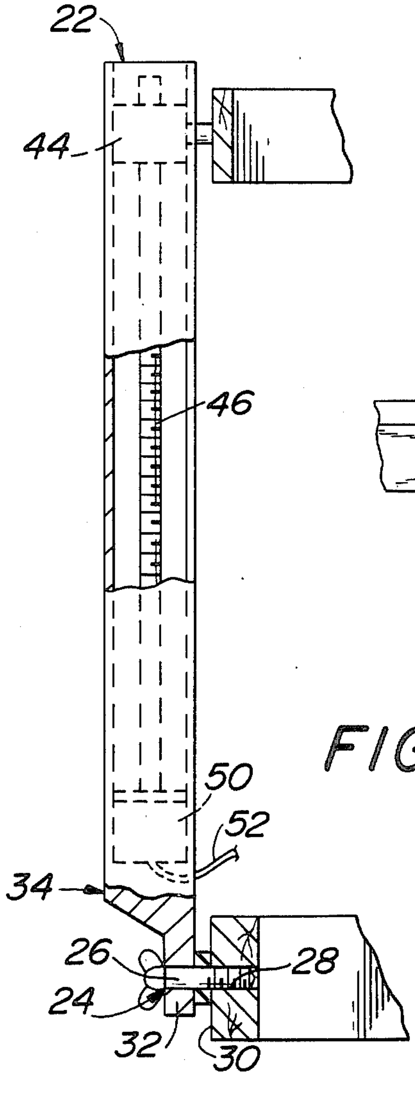
FIG. 5 is a fragmentary sectional view taken along line 5—5 of FIG. 4, with parts broken away to show details of construction.

Referring specifically to FIGS. 1, 4 and 5, the construction and arrangement of one of the table adjustment members 22 will be described in detail, it being understood that the other table adjustment member 22 is identical. As can be seen best in FIG. 5 the pivot connection 24 is provided by a threaded wing bolt 26 received within a threaded opening 28 extending into the side 30 of the lower horizontal support 16. This wing bolt passes through an opening in a lower end 32 of an outer housing 34 of the adjustment member 22 to pivotally secure the adjustment member to the support 16 when the platform 12 is intended to be positioned in an angular orientation relative to said support.

Referring specifically to FIGS. 4 and 5, the outer housing 34 of the adjustment member 22 includes spaced apart edges 40 defining an elongate channel 42 between them. An adjustable or moveable block 44 has a generally square cross-section conforming to the cross-section of the housing 34, and thereby is confined against rotation within said housing.

A rotatable screw 46 is received within a corresponding threaded opening 48 in the block 44. The lower end of the screw is secured to a reversible motor 50 so that it can be rotatably driven in opposite rotational directions.

As can be seen in FIGS. 1 and 5, an electrical conductor 52 extends from the motor 50, and this conductor is attached to an actuating switch 54 which can be reached easily by an individual undergoing traction therapy on the device 10. The switch 54 can be employed to operate the motor for rotating the screw 46 in either rotational direction.

As can be seen best in FIG. 4, a bolt 60 connects the adjustable body supporting platform 12 to the moveable block 44. Thus, when the screw 46 is rotated it causes the block 44 to move linearly along the screw, and this linear movement of the block is transmitted to the platform through the bolt 60 to cause a corresponding pivotal movement of the platform about the hinge 14.

It should be noted that the motor associated with the other table adjustment member likewise has an electrical conductor, and both conductors are directly connected to the actuating switch 54. As a result of this connection the actuation of the switch 54 affects operation of both motors 50 to thereby uniformly either raise or lower the body supporting platform 12, depending upon the direction of rotation of the screws 46.

Figure 2:
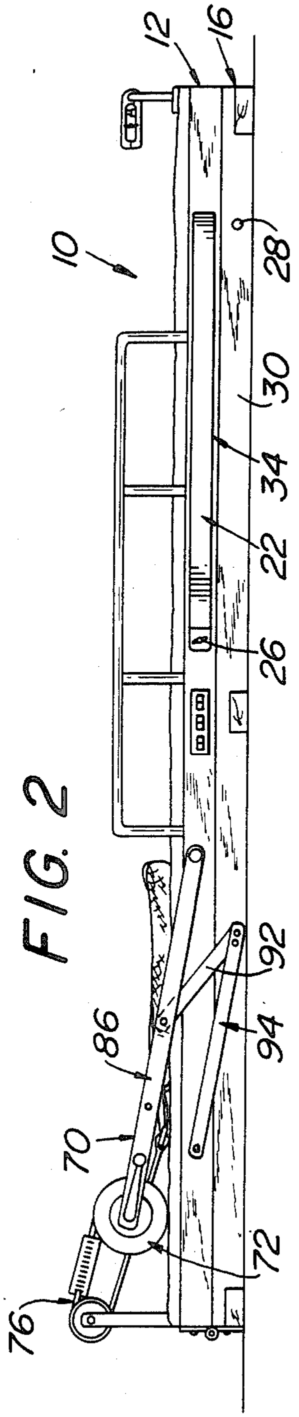
FIG. 2 is a side elevational view of the traction device shown in FIG. 1, but in a collapsed condition.

Referring specifically to FIGS. 1–3, the traction device 10 includes a hinged, collapsible system 70 through which a traction force is applied to an individual undergoing traction therapy. This system, which is a unique and important feature of the invention, is adapted to be maintained in a collapsed condition, as shown in FIG. 2, to permit a patient to easily position and secure himself or herself on the platform 12. Thereafter, with the individual properly positioned on the table, the hinged collapsible system 70 can be moved by the individual, or someone else, if desired, into its operative or active position shown in FIG. 1. With the system 70 in its active position the individual undergoing traction therapy can manually control the traction force applied to his or her body.

Referring to FIGS. 1–3, the hinged, collapsible system 70 includes a rotatable traction-force setting drum 72 to apply tension to a body-engaging harness, which in the illustrated embodiment is a neck and chin harness 74 adapted to be secured about the head of an individual undergoing traction therapy. However, it should be understood that other body-engaging harnesses can be utilized, such as one that is positioned about the chest or waist of the patient.

A cable assembly 76 interconnects the harness 74 to the rotatable drum 72, whereby manual rotation of the drum 72 either increases or decreases the traction force applied to the user. As can be seen best in FIG. 1 the cable assembly 76 includes a first cable segment 76A which is trained about the drum 72 and has its free end connected to a tension indicating spring member 78. A second cable segment 76B is connected to the opposite end of the spring 78, is trained about a rotatably mounted idler pulley 80, and has its opposed end connected to a safety link 82.

The safety link 82 is a metal or fiber member having a predetermined tensile strength for permitting the link to break, and thereby release any traction force, prior to the traction force exceeding an undesirably high level. The safety link can be a removable member for permitting its replacement with other safety links having different tensile strengths, depending upon the maximum acceptable traction force to be applied to the patient. A third cable segment 76C is connected to the opposite end of the safety line 82 and to the harness 74.

As can be seen best in FIGS. 1 and 2, the collapsible system 70 includes a pair of laterally spaced apart collapsible drum supports 86. Free ends 87 of these supports are positioned close to each other and are adapted to rotatably receive the drum 72 between them. A handle 88 constitutes an extension of the rotational axis of the drum, whereby manual rotation of the handle rotates the drum. A conventional ratchet mechanism is provided to lock the drum for maintaining the desired traction force, and for releasing the drum when it is desired to remove or reduce the applied traction force. Lower ends of the drum supports 86 are connected to the side walls of the platform 12 through pivot connections 90 to permit the supports to be moved between an inactive, collapsed condition, as shown in FIG. 2, and an operative, active position, as shown in FIG. 1.

Referring specifically to FIG. 1, each of the drum supports 86 is locked in its upright active position through a pair of locking links 92 and 94 (only one pair being illustrated in FIG. 1). Contiguous ends of the links 92 and 94 are pivotably joined together at 96, with the opposite end of link 92 being pivotably connected to the support 86, and the opposite end of the link 94 being pivotably connected to the side of the platform 12. The locking links 92 and 94 are maintained in their extended, locking position shown in FIG. 1 by the engagement of a spring biased pin or button 95 secured to link 94 engaging within a corresponding shaped opening in the link 92. In order to unlock and collapse the links into the inactive position shown in FIG. 2 the button 95 is manually depressed to release it from the opening. It is within the scope of this invention to employ other types of locking arrangements to retain the drum supports 86 in their upright and operative position, while permitting the supports to be collapsed into the position shown in FIG. 2, when desired.

Referring to FIGS. 1 and 2, it should be noted that when the device 10 is to be positioned in its collapsed condition, as shown in FIG. 2, the threaded wing bolt 26 is removed from the opening 28 in the side of the support 16 to thereby detach the housing 34 of the adjustment member 22 from said support. Thereafter the bolt 26 is employed to secure the lower end of the housing 34 directly to the platform 12 by securing the threaded end of the bolt 26 into a threaded passage 97 in the side of the platform (FIG. 1), with the housing 34 between said bolt and platform.

Figure 6:
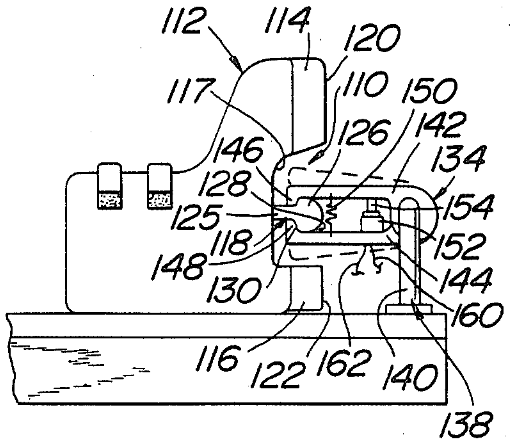
FIG. 6 is an enlarged side elevational view showing the manner in which a boot of this invention is secured to a traction device in accordance with this invention.

Referring specifically to FIGS. 1 and 6, the present invention employs a unique locking system 110 for securing the feet of an individual undergoing traction therapy onto the platform 12. This is an important feature of the invention, since it precludes the individual from sliding down the platform when the platform is oriented in an inclined position, with his or her head below his or her feet. This assists in the application of the desired tension force to the individual.

One unique feature of the locking system 110 resides in the construction of a pair of boots 112 (only one of which is shown in FIGS. 1 and 6) which are worn by the individual undergoing traction therapy. Each of the boots includes a built-up toe plate 114 and a built-up heel plate 116 to define an internal cavity 117 between them. An elongate, grippable member 118 is located in the region of the internal cavity, extends outwardly from the base thereof and terminates inwardly of the outer surfaces 120 and 122 of the toe plate 114 and heel plate 116, respectively. As a result of this construction an individual can put on the boots at a location remote from the traction device 10 and then walk to the device without the grippable member 118 engaging the ground.

Referring to FIG. 6, the grippable member 118 is of a unique construction, including a generally elongate, substantially cylindrical shaft section 125 extending outwardly from the base of the cavity 117, and an enlarged head 126 at the free end of said shaft section. The enlarged head has a generally convex outer curved surface 128 which joins the cylindrical shaft section 125 through a rearwardly facing shoulder 130.

Referring specifically to FIGS. 3 and 6, a pair of gripping members 134 are spaced laterally along a horizontal section 136 of a support rod 138. The support rod further includes vertically oriented end sections 140 which are secured within the upper surface of the platform 12.

As can be seen best in FIG. 6, each of the gripping members 134 includes a pair of jaws 142 and 144 rotatably joined to each other, with the horizontal section 136 of the support rod 138 constituting the pivot axle. Each of the jaws includes an inturned finger or tab 146, 148, respectively, for engaging behind the rewardly facing shoulder 130 formed at the junction between the enlarged head 126 and the cylindrical shaft section 125 of the grippable member 118. A tension spring 150 is secured between the jaws 142 and 144 to normally bias the jaws into a closed, gripping position, and a solenoid member 152 including a movable plunger 154 is positioned between the jaws. To insert the grippable member 118 of each boot 112 within its corresponding gripping member 134 the patient merely pushes the convex outer curved surface 128 of the enlarged head 126 inwardly against the spring loaded jaws 142 and 144. The convex curvature of the surface 128 forces the jaws 142 and 144 apart until the enlarged head 126 clears the inturned tabs 146, 148. Thereafter the jaws are forced toward each other by the spring 150 to engage behind the rearwardly facing shoulder 130 formed at the function of the shaft section 125 with the head 126.

As explained earlier, when an individual undergoing traction therapy is wearing the boots 112 and the boots are firmly secured within the gripping members 134, the individual is prevented from sliding downwardly along the platform, in the direction of arrow 158 in FIG. 1, when the patient is undergoing traction therapy in accordance with the preferred method of this invention.

It should be noted that the inturned fingers 146 and 148 of the rotatable jaws of the gripping member 130 have confronting, generally concave surfaces (not shown) conforming to the general circular shape of the cylindrical shaft section 125. As a result of this arrangement a patient undergoing traction therapy can easily shift his or her body relative to the line of action of the traction force by, in part, rotating his or her feet about the axes of the cylindrical shaft sections 125 of the boots 112. It generally is desirable for a patient to be able to move his or her body relative to the line of action of the traction force for the purpose of varying the location along which the traction force is to be concentrated. In other words, it often is desirable for the patient to be able to slightly rotate or move his or her body so that the line-of-action of the traction force is applied either to the patient's left side or right side, as needed.

As can be seen best in FIGS. 1 and 6, electrical conductors 160 and 162 are connected to respective solenoid members 152 of the gripping members 134, and, in turn, are connected to respective actuating switches 164 and 166 located within easy reach of an individual undergoing traction therapy, as illustrated in FIG. 1. This arrangement permits the patient to easily release himself from the platform by energizing the solenoid members 152 through actuation of the switches 164 and 166. When the solenoid members are energized the plungers 154 thereof will be moved outwardly to thereby bias the jaws 142 and 144 of the gripping members 134 into an open position, as shown in phantom representation in FIG. 6, against the opposing force of the tension spring 150. With the jaws in their open position the patient can easily remove the boots 112 from the gripping members 134, and thereby separate himself or herself from the traction device 10.

In accordance with the preferred method of using the traction device 10 the adjustment members 22 are secured to the horizontal support 16 through the pivot connection 24. Thereafter the motor 50 is actuated to fully retract the block 44 on the screw 46 to bring the platform 12 into a generally horizontal plane close to the horizontal support 16. In fact, the platform 12 will be in a position similar to that illustrated in FIG. 2; however, with the adjustment members 22 secured to the sides of the support 16, rather than to the sides of the platform 12.

In order to permit easy access to the device 10 the drum 72 and the drum supports 86 also are positioned in their collapsed position, as is illustrated in FIG. 2. With these elements in their collapsed position adjacent the hinge 14, the upper surface of the platform 12 generally is unobstructed to permit an individual to easily position himself or herself on the platform 12, without difficulty. As should be appreciated this is an important attribute of the invention, since a patient requiring traction therapy often is not very mobile, and therefore will require assistance to enter a traction device unless the device is designed to permit the patient to easily enter it without painfully contorting his or her body. As can be seen best in FIGS. 1-3, the device 10 includes laterally spaced apart handrails 143 having both horizontal and vertical elements to assist an individual in entering or leaving the device.

Before entering the traction device 10 the patient puts on the boots 112 so that he or she will be able to lock or secure himself or herself onto the platform 12 in the manner described earlier in this application. With the boots on, and while positioned on the platform, the individual can then pivot the drum 72 into an upright, operative position, as illustrated in FIG. 1, and thereafter lock the supports 86 to maintain the drum in its operative position.

With the patient firmly secured on the platform 12 he or she can then operate the table adjustment members 22 through actuation of the switch 54 to thereby raise the platform to the desired inclination. It should be understood that the harness 74 can be applied about the chin and neck of the patient prior to raising the platform, and at least a portion of the traction force can be applied through the harness while the individual is still in a horizontal orientation. However, the final tension force is set after the platform has been moved into its desired angular orientation, as shown in FIG. 1. With the individual oriented in the position shown in FIG. 1, the traction force is applied to the body, in part by the tension force imposed on the cable assembly 76 through actuation of the drum 72, and in part by the patient's own body weight.

As is well known, a person's body actually stretches, or lengthens, as it is undergoing traction therapy. Since the tension force applied to the body initially is set on the drum at the beginning of the traction therapy session, as the patient's body stretches on the fixed platform, the traction force being applied to the body actually reduces. In other words, in the present invention, the person undergoing traction therapy is a tensioned link between two fixed points (i.e., at the foot by gripping members 134, and at the head by rotatable drum 72) which do not move as the patient's body is being stretched.

Applicant has found that the overall traction force applied to the body by inclining the patient in a downwardly sloping arrangement, with his or her head below his or her feet, and with the further application of a tension force applied through a body engaging harness, provides extremely desirable tensioning of the full spinal area to assist in relieving spinal disfunctions and in restoring the lordotic curve.

The present invention is highly efficient in applying gentle stretching to both the muscles and ligaments in the spinal area, with the ability of the individual to slightly rotate or move his or her body to direct the stretching to predetermined locations in the spinal area. That is, the individual can actually rotate either to the left or to the right of the line of tension force to orient the line of force to the left or right side of the spinal area, as is desired. This is a very desirable feature of the present invention.

By employing safety line 82 in the cable assembly 76 an over zealous patient can be prevented from causing injury to himself or herself by attempting to apply excessive tension force to his or her body. In other words, if the individual attempts to apply excessive tension force to his or her body the safety link 82 will break to thereby prevent transmission of such an excessive force to the patient's body.

It also should be noted that the platform 12 preferably includes a polished metal upper surface, as opposed to a soft compressible surface such as a mattress. The use of such a polished surface permits the patient's own body weight to be employed effectively in the traction therapy, since frictional resistance between the patient and platform is minimized. This assists in applying the required stretching force to the lumbar and/or thoracic areas of the spine.

Figure 7:
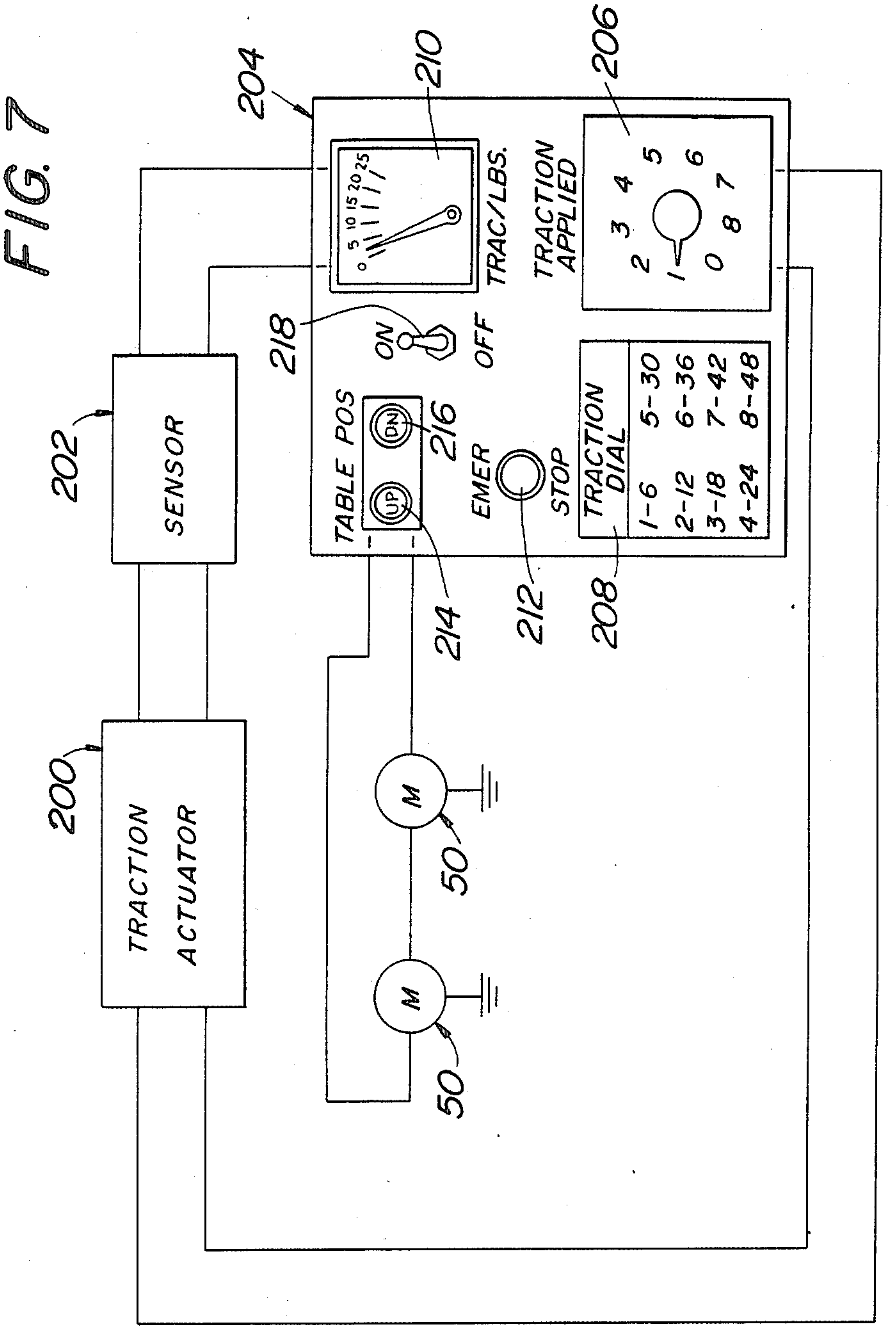
FIG. 7 is a schematic view of the circuit arrangement and control panel employed in the alternate embodiment of a traction device in accordance with this invention.

Referring to FIG. 7, and the elements shown in phantom in FIG. 1, an alternate embodiment of a traction device is illustrated for providing traction therapy in accordance with the preferred method of this invention. This device employs electronic components to control the application of the traction force, and is a more expensive device than the traction device 10 described earlier. However, an electronic traction device with more sophisticated controls may be desired or required for certain types of traction therapy, particularly for in-hospital or in-clinic usage. The traction device 10 described earlier is of a very simple construction, and has been designed with the idea in mind that an individual could actually employ such a traction device at home, without requiring assistance from others to administer traction therapy.

Turning specifically to FIGS. 1 and 7, a number of the elements of the device are identical to the elements employed in the device 10. However, in the alternate device the hinged collapsible system 70, including the traction setting drum 72 and the specific cable assembly 76 associated with the drum are omitted from the construction. In place of that arrangement the harness 74 is connected through suitable cable segments and the safety link 82 to a electronic traction actuator 200 through a traction sensing module 202. It should be noted that this arrangement can still take advantage of the rotatable pulley 80 for properly positioning the cable segment connected between the harness and the traction actuator 200.

As can be seen best in FIG. 7, a control panel 204 is provided with a dial 206 for setting the desired traction to be applied to the individual by the traction actuator 200. This dial includes numbers ranging from 0 through 8, and the amount of traction applied at each setting is shown on a scale 208 located to the left of the dial. Thus, as can be seen in FIG. 7, when the dial 206 is set to 1 a traction force of 6 lbs. will be applied by the traction actuator 200. In a similar manner, when the dial 206 is set to 4 a traction force of 24 lbs. will be applied by the traction actuator.

In order to be certain that the traction actuator 200 is applying the appropriate traction force to the patient's body the sensing module 202 is employed in the circuit for sensing the traction force applied by said actuator. The sensing module 202 transmits an electrical signal indicative of the traction force applied by the actuator 200 to a visual display 210 which converts the signal into a direct reading of the pounds of traction force being applied through the traction actuator.

As can be seen in FIG. 7 an emergency stop switch 212 is provided to permit a person monitoring the traction therapy to immediately deenergize the traction actuator if an undesirably high reading appears on the display 210, or if for any other reason it is decided to immediately abort the traction therapy.

As can be seen in FIG. 7, the control panel 204 further includes actuating buttons 214 and 216 for operating motors 50 to either raise or lower the platform 12. As described earlier these motors 50 form part of the actuating members 22. The control panel further includes a conventional on/off switch 218 to turn on and off all of the power to the traction device.

The control panel 204 can be located in an area remote from the traction platform so that an operator can monitor the traction treatment without the patient being aware of the specific manner in which such treatment is being controlled. Alternatively, it is possible to actually position the panel close to the platform 12 so that the individual undergoing therapy can control the entire operation. Thus, aside from the cost factor, an individual could self-administer his or her own traction therapy with the electronic device illustrated in FIG. 7, and therefore employ the device for in-home use.

In summary, Applicant has found that excellent results are achieved by applying tension to the upper part of the body while positioning the patient in a sloping position, with his or her head lower than his or her feet. In fact, Applicant has tested this type of therapy on himself, after failing to obtain adequate relief by conventional traction therapy techniques in which a weight was applied through a harness to his head while he was disposed in a generally horizontal orientation. The relief experienced by Applicant by use of the method of this invention was far greater than the relief achieved by the above-described conventional traction therapy technique.

Without further elaboration, the foregoing will so fully illustrate my invention that others may, by applying current or future knowledge, adopt the same under various conditions of service.

What is claimed is:

1. A method of administering traction therapy to an individual including the steps of supporting the individual on a body supporting platform inclined relative to a horizontal plane with the individual sloping downwardly in a direction from his or her feet to his or her head; securing the individuals feet to prevent linear movement of the individual along the downward slope of the platform; attaching a harness to an upper portion of the individuals body; and applying a force to the harness in said downwardly sloping direction, whereby traction is applied to the individual by a portion of the body weight of said individual and by said applied force.

2. The method of claim 1 including the step of attaching the harness to the individual's head.

3. The method of claim 1 including the step of positioning the body supporting platform so that it slopes in a downward direction at an acute angle to the horizontal plane.

4. The method of claim 1 including the step of connecting the harness to electronic tensioning means and actuating said electronic tensioning means for applying a force to the harness.

5. The method of claim 4 including the steps of sensing the force applied to the harness through the electronic tensioning means and providing a visually observable reading of the force.

6. The method of claim 1 including the steps of connecting the harness to a cable assembly, positioning the end of the cable assembly remote from the harness about a rotatable traction-force setting member that can be rotated by the individual undergoing traction therapy, whereby said individual can adjust the force applied to the harness through the cable assembly while undergoing traction therapy.

7. A traction device including a body supporting platform; pivot means for pivotally mounting said platform to a support member; table adjustment means for adjusting the angular positon of said platform relative to the support member by moving said platform about said pivot means; a cable assembly having one end adapted to be connected to a body engaging member and a second end adapted to be retained on a rotatable traction force-setting member; and to said platform for permitting pivotal movement of said support means from a first, active position in which the drum can be operated by an individual supported on the platform and receiving traction therapy, to a second, collapsed position for providing easy entry onto and exit from said platform.

8. The traction device of claim 7 including immobilizing gripping means connected to the device adjacent one end of the platform for preventing linear movement of an individual supported on the platform when said platform is positioned at an angle inclined to the horizontal plane.

9. The traction device of claim 8 wherein said immobilizing gripping means includes boots for receiving the feet of an individual lying on the platform, each of said boots having a lower surface and an elongate member projecting outwardly from said lower surface, gripping means retained on the device adjacent one end of the platform for gripping the elongate member of each boot to retain the individual on the table, and means actuatable by the individual for releasing the gripping means.

10. The traction device of claim 9 wherein the elongate member of each boot includes a generally cylindrical section projecting outwardly from the lower surface thereof, said generally cylindrically section terminating in an enlarged head, said gripping means including relatively movable jaw members for encircling said generally cylindrical section for permitting rotational movement of the boot about the axis of said generally cylindrical section but preventing said enlarged section from moving past said jaws to thereby prevent linear movement of said individual along the platform.

11. The traction device of claim 10 wherein each boot includes an outwardly projecting toe member and an outwardly projecting heel member on opposite sides of said elongate member, said elongate member terminating inwardly of outer surfaces of said toe and heel members, whereby an individual wearing said boots can walk on a horizontal supporting surface without said elongate member engaging said supporting surface.

12. The traction device of claim 7 including a safety link forming a part of said cable assembly, said safety link having a predetermined tensile strength and being adapted to break when said predetermined tensile strength is reached to prevent an excessive force from being transmitted to an individual undergoing traction therapy.

13. The traction device of claim 12 including a scale in said cable assembly for providing a visual reading of the force being applied through the cable assembly.

14. The traction device of claim 7 wherein said table adjustment means includes a motor means, a linearly movable member in association with said motor means and being linearly movable when said motor means is actuated; said linearly movable member being connected to said platform, whereby actuation of said motor means causes movement of said linearly movable member for adjusting the angular position of said platform.

15. The traction device of claim 7 wherein said body supporting platform has a polished upper surface for supporting the individual.

16. The traction device of claim 7 including locking means for locking said support means against pivotal movement when said support means is in said first, active position.

17. A traction device comprising a body supporting platform; pivot means for pivotally mounting said platform to a support member; table adjustment means for adjusting the angular position of said entire platform, as a single unit, relative to the support member by moving said entire platform about said pivot means to an inclined position for positioning the head of a patient lower than the feet of said patient when the patient is lying on said platform; a cable assembly having one end adapted to be connected to a body engaging member and a second end adapted to be connected to an electrically operated traction actuator, said traction actuator, when actuated, applying a force to said cable assembly and said body engaging member for applying a traction force to a patient in the direction of downward inclination of said platform; and force sensing means in said cable assembly for sensing the force applied to the body engaging member by the traction actuator and for transmitting a signal representative of said force to a display device for visually displaying the force applied to said body engaging member.

18. The traction device of claim 17 including traction setting means for setting the traction force to be applied to the body engaging member by the traction actuator.

19. The traction device of claim 17 including immobilizing gripping means connected to the device adjacent one end of the platform for preventing linear movement of an individual supported on the platform when said platform is positioned at an angle inclined to the horizontal plane.

20. The traction device of claim 19 wherein said immobilizing gripping means includes boots for receiving the feet of an individual lying on the platform, each of said boots having a lower surface and an elongate member projecting outwardly from said lower surface, gripping means retained on the device adjacent one end of the platform for gripping the elongate member of each boot to retain the individual on the table, and means actuatable by the individual for releasing the gripping means.

21. The traction device of claim 20 wherein the elongate member of each boot includes a generally cylindrical section projecting outwardly from the lower surface thereof, said generally cylindrically section terminating in an enlarged head, said gripping means including relatively movable jaw members for encircling said generally cylindrical section for permitting rotational movement of the boot about the axis of said generally cylindrical section but preventing said enlarged section from moving past said jaws to thereby prevent linear movement of said individual along the platform.

22. The traction device of claim 21 wherein each boot includes an outwardly projecting toe member and an outwardly projecting heel member on opposite sides of said elongate member, said elongate member terminating inwardly of outer surfaces of said toe and heel members, whereby an individual wearing said boots can walk on a horizontal supporting surface without said elongate member engaging said supporting surface.

23. The traction device of claim 17 including a safety link forming a part of said cable assembly, said safety link having a predetermined tensile strength and being adapted to break when said predetermined tensile strength is reached to prevent an excessive force from being transmitted to an individual undergoing traction therapy.

24. The traction device of claim 23 including a scale in said cable assembly for providing a visual reading of the force being applied through the cable assembly.

25. The traction device of claim 17 wherein said table adjustment means includes a motor means, a linearly movable member in association with said motor means and being linearly movable when said motor means is actuated; said linearly movable member being connected to said platform, whereby actuation of said motor means causes movement of said linearly movable member for adjusting the angular position of said platform.

26. A traction device comprising a body supporting platform; traction actuator means for applying a traction force to an individual supported on the platform; immobilizing gripping means connected to the device adjacent one end of the platform movable between a gripping position to engage a boot adapted to be worn by an individual receiving traction therapy, and an open position to release said boot; control means for moving said gripping means between said gripping position and open position and manually-operable actuating means remote from the gripping means and within easy reach of an individual lying on the supporting platform for permitting the individual to operate the control means to move said gripping means between said gripping and open positions while said individual is lying on said platform.

27. The traction device of claim 26 wherein said gripping means includes a pair of jaws for gripping an element of a boot intended to be worn by an individual undergoing traction therapy, and an open position to release the element of the boot.

28. A traction device including a boot to be worn by an individual undergoing traction therapy and a gripping means connected to the device adjacent one end of a platform on which an individual to receive traction therapy is intended to be supported by lying flat on said platform, said boot including a lower surface having a toe member and a heel member with a cavity positioned therebetween, an elongate member projecting outwardly from a lower surface of the cavity and terminating inwardly of outer surfaces to said tow member and heel member, said gripping means including gripping members movable between a first postion for gripping the elongate member and a second position for releasing the gripping action on the elongate member, control means for moving the gripping members between said first and second positions and manually-operable actuating means remote from the gripping members and within easy reach of an individual lying on the supporting platform for permitting the individual to operate the control means to move said gripping members between said gripping and open positions while said individual is lying on said platform.

29. The device of claim 28 wherein the elongate member includes a generally cylindrical section projecting outwardly from the lower surface of the cavity, said generally cylindrical section terminating in an enlarged section, said gripping means including relatively movable jaw members movable to a first, closed, gripping position for encircling said generally cylindrical section to thereby permit rotational movement of the boot along the elongate axis of said generally cylindrical section but preventing said enlarged section from moving outwardly beyond the jaws to thereby prevent linear movement of said individual along the platform, said jaws being movable to a second, opened position in which the enlarged section of the elongate member can be removed from between said jaw members.

30. The device of claim 29 including spring means for normally biasing said jaw members into a closed position and actuating means for moving the jaws into an open position against the action of the force applied by the spring means.

31. A method of administering traction therapy to an individual including the steps of supporting the individual on a body supporting platform inclined relative to a horizontal plane with the individual sloping downwardly in a direction from his or her feet to his or her head; securing the individual's feet at a fixed location relative to the platform to prevent linear movement of the individual along the downward slope of the platform; attaching a harness to an upper portion of the individual's body; and applying a force to the harness in said downwardly sloping direction at a fixed location which does not move during the administration of traction therapy to the individual, whereby said individual constitutes a tensioned link between the fixed location at which the individual's feet are secured and the fixed location at which the force is applied.

32. The method of claim 31 including the steps of connecting the harness to a cable assembly, positioning the end of the cable assembly remote from the harness about a rotatable traction-force setting member that can be rotated by the individual undergoing traction therapy, whereby said individual can adjust the force applied to the harness through the cable assembly while undergoing traction therapy.

* * * * *